United States Patent [19]

Berry

[11] Patent Number: 5,306,240

[45] Date of Patent: Apr. 26, 1994

[54] TUNNELER AND METHOD FOR IMPLANTING SUBCUTANEOUS VASCULAR ACCESS GRAFTS

[75] Inventor: William Berry, Pasadena, Tex.

[73] Assignee: Pilling Co., Fort Washington, Pa.

[21] Appl. No.: 7,245

[22] Filed: Jan. 21, 1993

[51] Int. Cl.$^5$ .............................................. A61B 19/00
[52] U.S. Cl. ...................................... 604/51; 604/49; 604/272; 604/8; 606/108
[58] Field of Search ....................... 606/108, 167, 185; 604/4, 8, 49, 51, 52, 53, 164, 170, 264, 272, 274

[56] References Cited

U.S. PATENT DOCUMENTS

| | | | |
|---|---|---|---|
| 3,640,281 | 2/1972 | Robertson | 604/49 |
| 4,431,426 | 2/1984 | Groshong et al. | 604/164 |
| 4,453,928 | 6/1984 | Steiger | 604/264 |
| 4,574,806 | 3/1986 | McCarthy | 606/108 |
| 4,684,369 | 8/1987 | Wildemeersch | 604/272 |
| 4,792,326 | 12/1988 | Beck et al. | 604/272 |
| 4,832,687 | 5/1989 | Smith, III | 604/51 |

FOREIGN PATENT DOCUMENTS

| | | | |
|---|---|---|---|
| 37701 | 12/1886 | Fed. Rep. of Germany | 606/185 |
| 218921 | 2/1910 | Fed. Rep. of Germany | 606/167 |
| 619110 | 9/1935 | Fed. Rep. of Germany | 604/272 |
| 322195 | 11/1971 | U.S.S.R. | 604/272 |

OTHER PUBLICATIONS

IMPRA publication entitled "Impra Kelly-Wick Access Tunneler Set KW2000" TU 304,691, ©1990.
IMPRA publication entitled "Impra Kelly-Wick Tunneler Set" PT 125.591, ©1989.
The Merck Manual of Diagnosis and Therapy, Fifteenth Edition, "Extracorporeal Procedures" pp. 1576-1577 (1987).
Better Homes and Gardens New Family Medical Guide, "Kidney and Urinary System" pp. 540-542 (1982).

*Primary Examiner*—Ralph Lewis
*Attorney, Agent, or Firm*—Howson & Howson

[57] ABSTRACT

An improved tunneler for placement of an arteriovenous graft in subcutaneous tissue of a patient, includes a shaft with opposite ends carrying a penetrating tip and a handle. The shaft is manually bendable but has sufficient rigidity for retaining a desired curvature when in use. The tip and handle are interchangeable. In implanting a graft, the shaft is passed through an incision near the distal end of a patient's limb to a proximal incision, to form a first tunnel. With the shaft in place in the tunnel, the tip and handle are interchanged, and a graft is attached to the tip and pulled toward the proximal incision until its end is exposed. A second tunnel is then formed, again by passing the instrument through the distal incision toward the proximal incision. The tip and handle are again interchanged, and, with the tip attached to the other end of the graft, the graft is pulled into place to form a loop.

8 Claims, 2 Drawing Sheets

TUNNELER AND METHOD FOR IMPLANTING SUBCUTANEOUS VASCULAR ACCESS GRAFTS

BRIEF SUMMARY OF THE INVENTION

This invention relates generally to surgical instruments, and more particularly to instruments known as "tunnelers", used for subcutaneous placement of arteriovenous grafts for extracorporeal circulation of the blood, arterial bypasses, and the like.

Subcutaneous arteriovenous grafts are used in various peripheral vascular or blood access procedures such as arterial bypasses in the extremities and extracorporeal circulation for hemodialysis and hemofiltration. When native vasculature is insufficient for an endogenous arteriovenous fistula, exogenous prosthetic grafts made from an expanded PTFE (polytetrafluoroethylene) or bovine carotid are common substitutes. For long-term hemodialysis or hemofiltration, the forearm of the patient may be fitted with a long access graft anastomosed between the radial artery and the cephalic vein near the elbow, and extending, in a loop, toward the wrist. This arrangement provides a range of sites, over the length of the forearm, for repetitive tapping off and returning the blood.

Subcutaneous placement of the graft is accomplished with a tunneler which typically comprises a curved shaft with a bullet-like penetrating tip at one end and a handle permanently fixed to the other end. The tip is typically removably connected to the shaft so that it can be interchanged with other tips of different sizes.

The tunneler must be manipulated with great care to insure precise placement of the graft in depth and latitude and to avoid excessive trauma and other complications.

Typically, incisions are made in the lower and upper anterior regions of the forearm. A tip, appropriate for the size of graft to be implanted, is attached to the shaft and introduced through the lower incision, i.e. the incision nearest the wrist. The handle is manipulated to guide the tip up through the forearm and out through the upper incision, thereby forming a first subcutaneous tunnel.

The length of the graft is more than twice the distance between the incisions. One end of the graft is secured, by a surgical ligature, to the exposed tip of the tunneler and the graft is then drawn back through the tunnel until a sufficient portion of the graft extends from the lower incision to loop back to the upper incision. The instrument is then disconnected from the graft, and introduced through the upper incision, and the handle manipulated, once again, to guide the tip downward through the forearm, and out through the lower incision, to form a second subcutaneous tunnel. The free end of the portion of the graft extending from the lower incision is connected to the tip of the instrument, and, by drawing the instrument upward, the graft is looped back up through the second tunnel. Finally, the ends of the graft are anastomosed to the artery and vein, respectively, and the incisions sutured. Similar tunneling procedures have been used for femoral loop access grafts.

One problem with the conventional procedure described above is that the second tunnel, made by moving the instrument in the direction from the elbow toward the wrist, is more difficult to form than is the first tunnel, which is made by moving the instrument in the direction from the wrist toward the elbow. Tunnel depth is an important consideration, and is particularly difficult to control when the instrument is moved in the direction from the elbow toward the wrist.

Another problem with the conventional procedure is that, in the formation of each tunnel, the instrument moves in a first direction, and the graft is pulled into the tunnel in the opposite direction. These opposite movements tend to cause a great deal of trauma to the patient.

Still another problem with the conventional procedure is that the entire portion of the graft which is looped back through the second tunnel must first be pulled through the first tunnel. This also results in excessive trauma in the first tunnel.

With the conventional procedure, there is also a substantial likelihood that kinks, which tend to cause thrombosing, will form in the graft.

The general object of the invention is to provide a novel and improved tunneling instrument and method which overcome the aforementioned problems.

A further object of the invention to provide an improved tunneler for simplified placement of a subcutaneous loop access graft for extracorporeal circulation of the blood.

Another object is to provide an improved tunneler for implanting a subcutaneous loop access graft in a patient with minimal risk of trauma or other complications.

Still another object of the invention is to provide an improved method for placement of a subcutaneous graft by tunneling, which is simpler to carry out than prior methods, which results in better control of the tunnel depth, and which produces less trauma and is less likely to result in complications.

These and other objects and aspects of the invention are accomplished with a novel and improved tunneler comprising a long shaft with a penetrating tip at one end interchangeable with a handle at the other end. The tip is also interchangeable with tips of other sizes to suit requirements, and the shaft is constructed of a relatively stiff metal sufficiently malleable for bending manually to a desired tunnel curvature.

The interchangeability of the tip and handle makes it possible to implant a subcutaneous arterio-venous vascular access graft by the steps of: forming a first subcutaneous tunnel by pushing a tunnelling instrument, comprising a rod having a tunnelling tip at one end and a handle at its other end, through an incision adjacent to a patient's hand toward the patient's elbow until said one end of the rod projects through an incision near the patient's elbow and said other end of the rod projects outwardly from the incision near the patient's hand; removing the tunnelling tip and handle from the rod, connecting the tunnelling tip to said other end of the rod and connecting the handle to said one end of the rod, whereby the positions of the handle and tip on said rod are interchanged; attaching the graft to the tunnelling tip; pulling the graft through the first subcutaneous tunnel, by moving the rod through said tunnel in the direction from the patient's hand toward the patient's elbow, until one end of the graft projects through said incision near the patient's elbow and a length of the graft, having a free end, extends from said incision near the patient's hand; forming a second subcutaneous tunnel by pushing the tunnelling instrument, with the tunnelling tip attached to the leading end thereof and the handle attached to the trailing end thereof, through said incision adjacent to the patient's hand toward the patient's elbow until said leading end projects through an incision near the patient's elbow; again removing the tunnelling tip and handle from the rod and interchanging the positions of the handle and tip on said rod; attaching said free end of the portion of said length of the graft to the tunnelling tip; pulling said graft through said second subcutaneous tunnel, by moving the rod through said second tunnel in the direction from the patient's hand toward the patient's elbow, until said free end of the graft projects through the last-mentioned incision near the patient's elbow, whereby the graft takes the form of a loop; and connecting one end of said graft to an artery of the patient and connecting the other end of said graft to a vein of the patient.

By using the foregoing method, the surgeon avoids the necessity of pulling, through the first tunnel, the portion of the graft which is to be implanted in the second tunnel. The method also enables the surgeon to form both tunnels by passing the instrument from the incision nearest the patient's hand toward the incision near the patient's elbow. It also enables the surgeon to pull the graft into each tunnel in the direction in which the tunneler moved when the tunnel was formed, thereby eliminating excessive trauma.

Other objects, details and advantages of the invention, will be more fully understood from the following detailed description, when read in conjunction with the accompanying drawings.

DETAILED DESCRIPTION

Figure 1:
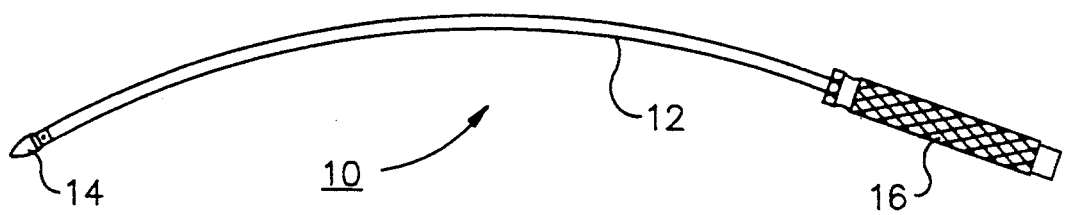
FIG. 1 is an elevational view of a tunneler according to the invention for subcutaneous placement of a prosthetic arteriovenous graft.
Figure 2:
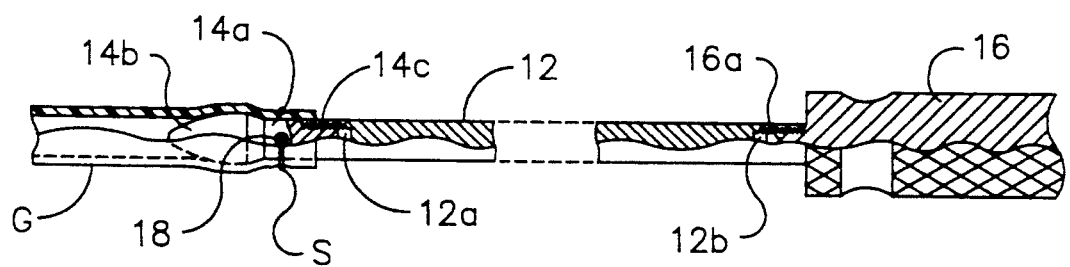
FIG. 2 is a fragmentary view, partly in longitudinal cross-section, of the tunneler of FIG. 1 with a prosthetic graft ligated to one end.

Referring now to the drawings wherein like referenced characters designate like or corresponding parts throughout the several views, FIG. 1 represents a tunneler 10 constructed according to the invention. The tunneler includes a shaft 12, having a circular transverse cross-section, with a penetrating tip 14 at one end and a knurled handle 16 at the other end. Shaft 12 is typically 4 or 5 mm. in diameter and is preferably made of a non-heat treated malleable metal, such as 300 Series stainless steel, having sufficient stiffness to retain a curvature manually formed for a desired tunnel path. As shown in FIG. 2, the opposite ends of shaft 12 have identical, but oppositely facing, internally threaded bores 12a and 12b, each being capable of coaxially receiving either tip 14 or handle 16.

Tip 14 comprises a cylindrical section 14a, an enlarged diameter bullet-shaped head 14b on one end of section 14a, and a reduced diameter threaded shank 14c coaxially extending from the opposite end of section 14a. Different tips can have heads of different diameters in order to form tunnels of the appropriate sizes for the grafts selected for implant. The diameter of head 14b will typically fall in the range from 6 mm. to 10 mm. The diameter of the section 14a and the outer diameter of shaft 12 are preferably the same to provide flush surfaces where they join. The external threads of shank 14c are engageable with the internal threads of either bores 12a and 12b. A transverse hole 18 through the middle of section 14a provides means for positively securing an end of a graft G to tip 14 with a ligature S. Preferably the graft is attached to the tip by inserting the tip into the end of the graft, passing the ligature through the graft and hole 18, and tying. Handle 16 is circular in cross section and knurled to provide a non-slip grip. An externally threaded shank 16a extends from handle 16 and is engageable in either of threaded bores 12a and 12b. Since the tip 14 and handle 16 have similar threaded shanks, they are interchangeable in that the tip and handle can each be attached to either end of shaft 12.

Figure 3A:
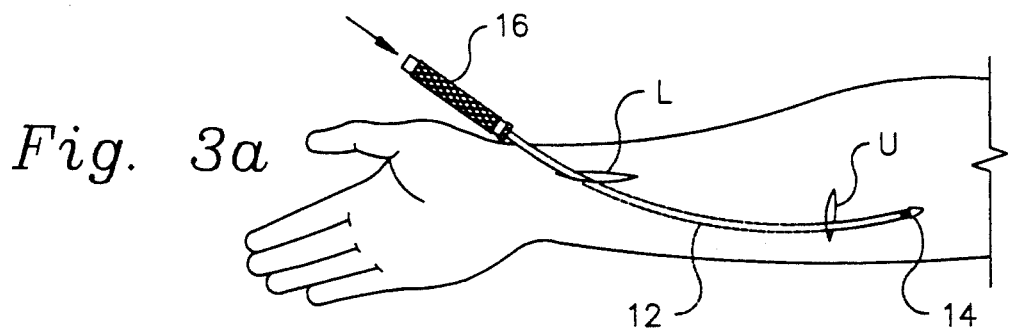
FIGS. 3a-3e are elevational views showing the anterior region of a patient's forearm, and representing stages in sequence of a tunneling procedure utilizing the tunneler of FIG. 1.
Figure 3B:
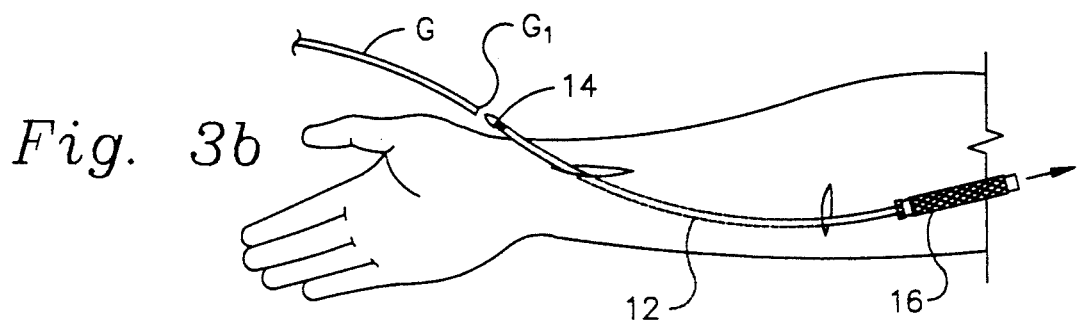
Figure 3C:
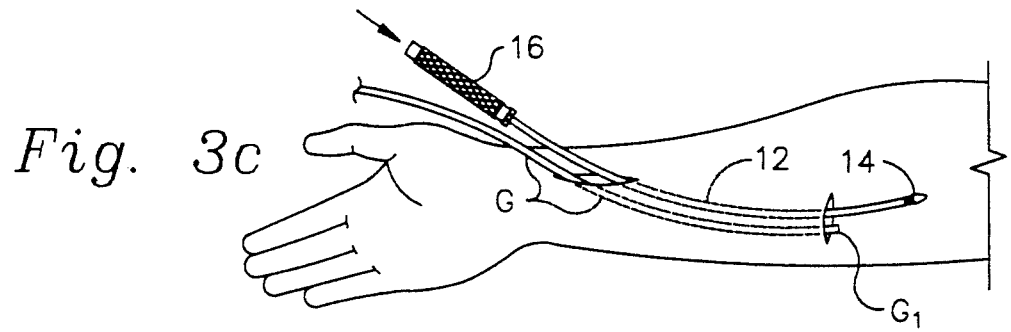
Figure 3D:
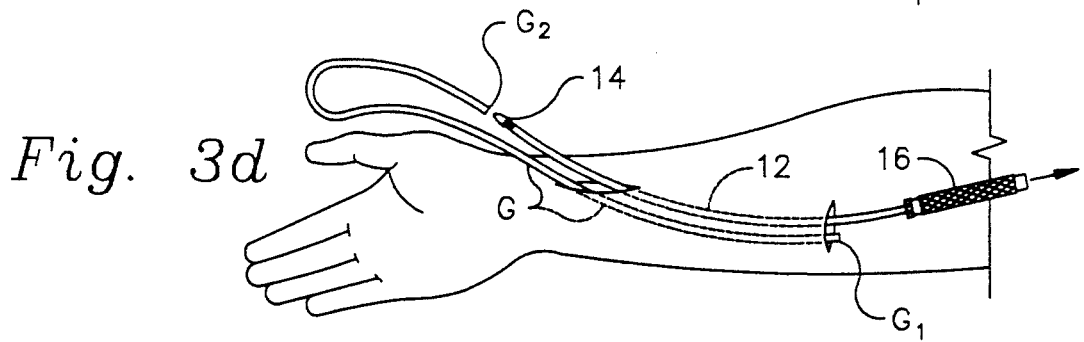
Figure 3E:
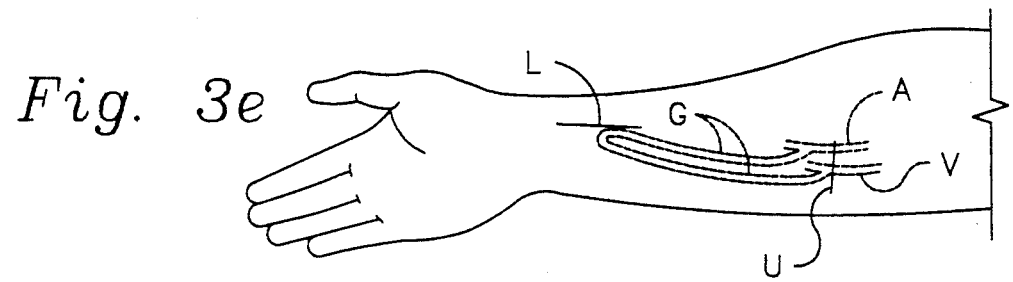

The procedure for placing a loop access graft in the forearm of a patient will now be described with reference to FIGS. 3a-3e. Incisions L and U are made respectively in the lower and upper anterior regions of the forearm. Tunneler 10 is inserted through lower incision L and manipulated by handle 16 until tip 14 is exposed at the upper incision U as shown in FIG. 3a to form a first subcutaneous tunnel. With shaft 12 remaining in position, tip 14 and handle 16 are switched on the ends of shaft 12 as shown in FIG. 3b, and one end $G_1$ of graft G is positively secured to tip 14 by a ligature S, as shown in FIG. 2, fastened around the graft and through hole 18 in section 14a of the tip. The graft is then drawn through the first subcutaneous tunnel to upper incision U, where the exposed tip 14 is unfastened from graft end $G_1$. Tunneler 10 is reintroduced through lower incision L and guided through the forearm until tip 14 is again exposed at upper incision U, as shown in FIG. 3c, to form a second subcutaneous tunnel. Tip 14 and handle 16 are switched again on the ends of shaft 12, as shown in FIG. 3d. The other end $G_2$ of graft G is ligated to tip 14 and drawn through the second subcutaneous tunnel toward upper incision U until exposed, and the loop in graft G is pulled into lower incision U. The graft is then unfastened from tip 14, and ends $G_1$ and $G_2$ are appropriately dressed and connected in side-to-side fashion to the radial artery A and cephalic vein V, and the incisions closed, as shown in FIG. 3e.

Two important aspects of the procedure afforded by the present invention should be noted in particular. The critical steps of guiding tip 14 through the forearm is always accomplished with handle 16 at the outer extremity of the forearm, and only the length of graft required within each tunnel is drawn through the forearm. Heretofore, it was necessary to draw the entire length of the graft allocated for the second tunnel through the first tunnel before drawing it into the second tunnel thus increasing the risk of trauma. Further, the bendable shaft enables the surgeon to shape curvature of the tunneler to accommodate variations in arm size and shape as well as any personal preference of the surgeon.

Various modifications can be made to the invention as described above. For example, the graft can be temporarily secured to the shaft by a length of suture material, without inserting the tip into the end of the graft. In another modification, instead of providing hole 18 in the tip, holes performing a similar function can be provided near both ends of shaft 12. In still another modification, the shaft can be provided with external threads, while the tip and handle are provided with internal threads. While the method described herein will ordinarily be carried out using a single instrument, it can be carried out using two separate instruments, one for forming the first tunnel and the other for forming the second tunnel.

It will be understood that various other changes in the details, steps and arrangement of parts which have been herein described and illustrated in order to explain the nature of the invention, may be made by those skilled in the art within the principle and scope of the invention as expressed in the appended claims.

I claim:

1. A method of implanting a subcutaneous graft for vascular access comprising the steps of:

forming a subcutaneous tunnel by pushing a tunnelling instrument, comprising a rod having a tunnelling tip at one end and a handle at its other end, through a first incision until said one end of the rod projects through a second incision remote from said first incision and said other end of the rod projects outwardly from the first incision;

removing the handle from said other end of the rod and attaching said handle to said one end of the rod;

attaching an end of the graft to the rod with said end of the graft being adjacent to said other end of the rod; and pulling the graft through said subcutaneous tunnel, by moving the rod through said tunnel, in the direction from said first incision toward said second incision.

2. The method according to claim 1 further comprising the steps of:

removing the tunnelling tip from said one end of the rod; attaching the tunneling tip to the other end of the rod in place of said handle; and attaching said one end of the graft to said tunnelling tip.

3. The method according to claim 1 wherein, in said pulling step, the graft is moved through said tunnel until said one end of the graft projects from said second incision.

4. A method of implanting a subcutaneous, arteriovenous graft for vascular access comprising the steps of:

forming a first subcutaneous tunnel by pushing a tunnelling instrument, comprising a rod having a tunnelling tip at one end and a handle at its other end, through an incision adjacent to a patient's hand toward the patient's elbow until said one end of the rod projects through an incision near the patient's elbow and said other end of the rod projects outwardly from the incision near the patient's hand;

removing the tunnelling tip and handle from the rod, connecting the tunnelling tip to said other end of the rod and connecting the handle to said one end of the rod, whereby the positions of the handle and tip on said rod are interchanged;

attaching the graft to the tunnelling tip;

pulling the graft through said first subcutaneous tunnel, by moving the rod through said tunnel in the direction from the patient's hand toward the patient's elbow, until one end of the graft projects through said incision near the patient's elbow and a length of the graft, having a free end, extends from said incision near the patient's hand;

forming a second subcutaneous tunnel by pushing a tunnelling instrument, comprising a rod having a tunnelling tip at one end and a handle at its other end, with the tunnelling tip attached to the leading end thereof and the handle attached to the trailing end thereof, through said incision adjacent to the patient's hand toward the patient's elbow until said leading end projects through an incision near the patient's elbow;

removing the tunnelling tip and handle from the last-mentioned rod and interchanging the positions of the handle and tip on the last-mentioned rod;

attaching said free end of the portion of said length of the graft to the tunnelling tip on the last-mentioned rod;

pulling said graft through said second subcutaneous tunnel, by moving the last-mentioned rod through said second tunnel in the direction from the patient's hand toward the patient's elbow, until said free end of the graft projects through the last-mentioned incision near the patient's elbow, whereby the graft takes the form of a loop; and connecting one end of said graft to an artery of the patient and connecting the other end of said graft to a vein of the patient.

5. A method for placing a loop access graft in the forearm of a patient with a tunneler, the tunneler having a shaft, and a tip and a handle interchangeable on opposite ends of the shaft, comprising the steps of:

incising lower and upper anterior regions of the forearm;

by manipulating the handle, introducing the tunneler into the lower incision until the tip is exposed at the upper incision to form a first tunnel;

interchanging the tip and handle on the shaft;

fastening one end of the graft to the tip;

by manipulating the handle, withdrawing the tunneler from the first tunnel until the one end of the graft is exposed at the upper incision; and unfastening the one end of the graft from the tip.

6. A method according to claim 14 further comprising the steps of:

by manipulating the handle, introducing the tunneler into the lower incision until the tip is exposed at the upper incision to form a second tunnel;

interchanging the tip and handle on the shaft;

fastening the other end of the graft to the tip;

by manipulating the handle, withdrawing the tunneler from the second tunnel until the other end of the graft is exposed at the upper incision and a loop, formed in the graft by withdrawing the tunneler from the second tunnel, is pulled into the lower incision; and anastomosing the respective ends of the graft to the radial artery and cephalic vein in the upper region of the forearm and closing the incisions.

7. A method for placing a loop access graft in between distal and proximal regions of a patient's extremity with a tunneler, the tunneler having a shaft, and a tip and handle interchangeable on opposite ends of the shaft, comprising the steps of:

by manipulating the handle, introducing the tunneler into the distal region until the tip is exposed at the proximal region to form a first tunnel;

interchanging the tip and handle on the shaft;

attaching one end of the graft to the tip;

by manipulating the handle, withdrawing the tunneler from the first tunnel until the one end of the graft is exposed at the proximal region; and detaching the graft from the tip.

8. A method according to claim 7 further comprising the steps of:

by manipulating the handle, introducing the tunneler into the distal region until the tip is exposed at the proximal to form a second tunnel;

interchanging the tip and handle on the shaft;
attaching the other end of the graft to the tip;
by manipulating the handle, withdrawing the tunneler from the second tunnel until the other end of the graft is exposed at the proximal end and the loop end is at the distal region; and
anastomosing the ends of the graft respectively to the adjacent artery and vein.

* * * * *